US006475174B1

(12) United States Patent
Chow

(10) Patent No.: US 6,475,174 B1
(45) Date of Patent: Nov. 5, 2002

(54) DORSAL COMPARTMENT BRACE

(76) Inventor: James C. Y. Chow, 4121 Veterans Memorial Dr., Mount Vernon, IL (US) 62864

( * ) Notice: Subject to any disclaimer, the term of this patent is extended or adjusted under 35 U.S.C. 154(b) by 0 days.

(21) Appl. No.: 10/032,840

(22) Filed: Oct. 25, 2001

(51) Int. Cl.[7] .............................. A61F 5/00; A61F 13/00
(52) U.S. Cl. ................. 602/5; 602/21; 602/64
(58) Field of Search .............................. 602/20, 21, 12, 602/5, 14, 26, 27, 64; 128/878, 879; 2/16, 256, 161.1, 162

(56) References Cited

U.S. PATENT DOCUMENTS

| 4,602,620 | A | | 7/1986 | Marx | |
|---|---|---|---|---|---|
| 4,612,925 | A | * | 9/1986 | Bender | 128/877 |
| 4,706,658 | A | * | 11/1987 | Cronin | 128/DIG. 20 |
| 4,709,694 | A | * | 12/1987 | O'Connell | 2/167 |
| 4,913,755 | A | * | 4/1990 | Grim | 156/145 |
| 5,513,657 | A | * | 5/1996 | Nelson | 128/879 |
| 5,514,081 | A | * | 5/1996 | Mann | 128/DIG. 20 |
| 5,591,121 | A | * | 1/1997 | Cantrell | 602/20 |
| 5,759,166 | A | * | 6/1998 | Nelson et al. | 602/21 |
| 5,772,620 | A | | 6/1998 | Szlema et al. | |
| 5,876,363 | A | | 3/1999 | Marx | |
| 6,029,277 | A | * | 2/2000 | Picchione, II | 2/16 |
| 6,120,471 | A | | 9/2000 | Varn | |
| 6,146,347 | A | | 11/2000 | Porrata | |
| 6,213,969 | B1 | * | 4/2001 | MacMorran et al. | 602/21 |

FOREIGN PATENT DOCUMENTS

| CH | 667397 A5 | * | 10/1988 | ........... A63B/71/14 |
|---|---|---|---|---|
| DE | 3631253 A1 | * | 3/1988 | ........... A61F/13/10 |

* cited by examiner

Primary Examiner—Michael A. Brown
Assistant Examiner—Fenn C Mathew
(74) Attorney, Agent, or Firm—Polster, Lieder, Woodruff & Lucchesi, L.C.

(57) ABSTRACT

A dorsal compartment brace (10) includes a sleeve (12) having an open end (14) sized to fit over the person's arm (A) and extend above the person's wrist. The opposite end (16) of the sleeve has openings (18) and an extension (19) through which the thumb and fingers of the person's hand extend. A splint (20) carried in the sleeve is contoured to fit about the rear, dorsal portion of the person's hand. When the sleeve is worn, the splint immobilizes the first dorsal compartment of the hand to facilitate rehabilitation of the hand.

10 Claims, 1 Drawing Sheet

DORSAL COMPARTMENT BRACE

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to orthotic devices; and more to particularly, to a dorsal compartment brace for use in immobilizing the first dorsal compartment of the hand.

The dorsal portion of a person's hand includes the tendons and muscles adjacent the thumb and in the area of the carpal bones forming the back of the hand. This portion of the hand is subject to tendon and muscle damage usually resulting from a repetitive motion injury. While such injuries can be surgically repaired, a more conservative, non-invasive treatment is to immobilize this portion of the hand and let the tendons and muscles heal without resort to surgery. One way of achieving this is to have the patient wear an orthotic device or appliance which immobilizes the dorsal portion of the hand, while preferably not unduly effecting the person's use of the rest of their hand.

Orthotic devices for the hand and wrist are known in the arts. See, for example, U.S. Pat. No. 6,146,347, 6,120,471, 5,876,363, 5,772,620, and 4,602,620. There are a number of problems with the orthotic devices shown in these patents and other conventional devices. In particular, they are cumbersome to wear, often requiring wires or straps to put on and adjust. Second, they are not comfortable to wear. Because of their size and all the ancillary parts they involve, they are difficult, if not impossible, to wear underneath a shirt or blouse. For example, the various wires and straps employed on these prior art braces can snag and rip clothing. It can also scratch and irritate the wearer, particularly if the device is worn while the person is sleeping. Finally, because of all the wires or straps, the devices call attention to the fact the wearer has suffered an injury.

Accordingly there is a need for a dorsal compartment brace which is easy to put on and take of, is comfortable to wear, does not require tedious adjustments and immobilizes the dorsal compartment of the wearer's hand for rehabilitation purposes so to provide an orthopedic function, and has a cosmetically pleasing appearance as well so as to be unobtrusive.

BRIEF SUMMARY OF THE INVENTION

In accordance with the invention, a dorsal compartment brace includes a sleeve open at one end to fit over the wearer's hand and extend some distance up their arm. The other end of the sleeve is has spaced openings which allow the fingers of the hand to be inserted through this end of the sleeve. A stiffening member comprising a splint is fitted into the portion of the brace which fits over the dorsal or rear portion of the wearer's hand. The splint extends from approximately the first joint of the thumb back along the outer portion of the wrist. The splint is sufficiently rigid so as to keep the first dorsal compartment of the person's hand and wrist immobilized. The brace otherwise allows the wearer use of their hand, but immobilizing the first dorsal compartment facilitates healing and rehabilitation, without resort to surgery. The sleeve is of a relatively thin, lightweight, skin colored material that is easy to put on and remove and is unobtrusive in appearance. No straps are required to hold the brace in place or to adjust it to the wearer's hand, and the brace fits comfortably beneath the sleeve or a shirt or coat. Other objects and features will be in part apparent and in part pointed out hereinafter.

BRIEF DESCRIPTION OF THE SEVERAL VIEWS OF THE DRAWINGS

The objects of the invention are achieved as set forth in the illustrative embodiments shown in the drawings which form a part of the specification.

Corresponding reference characters indicate corresponding parts throughout the several views of the drawings.

DETAILED DESCRIPTION OF INVENTION

Figure 1:
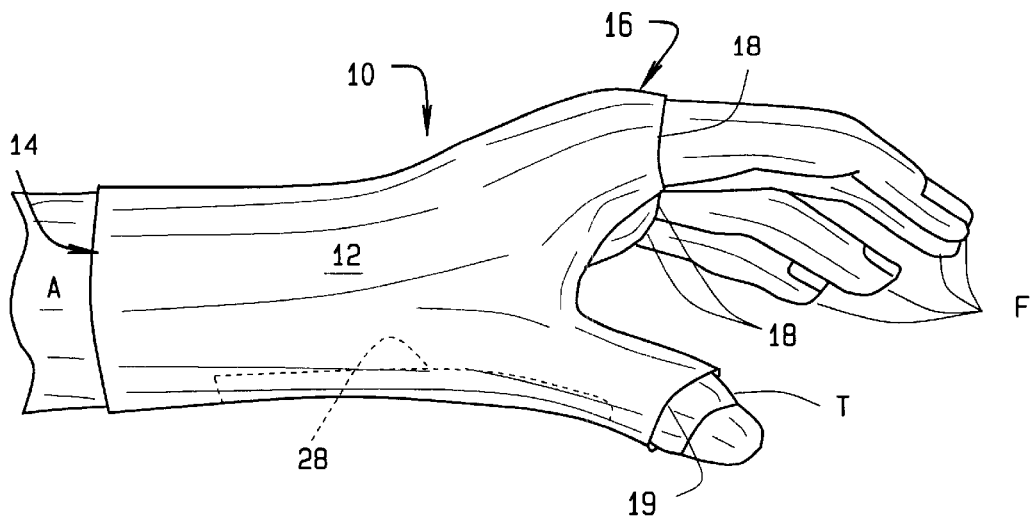
FIG. 1 is a perspective view of a dorsal compartment brace of the present invention.
Figure 2:
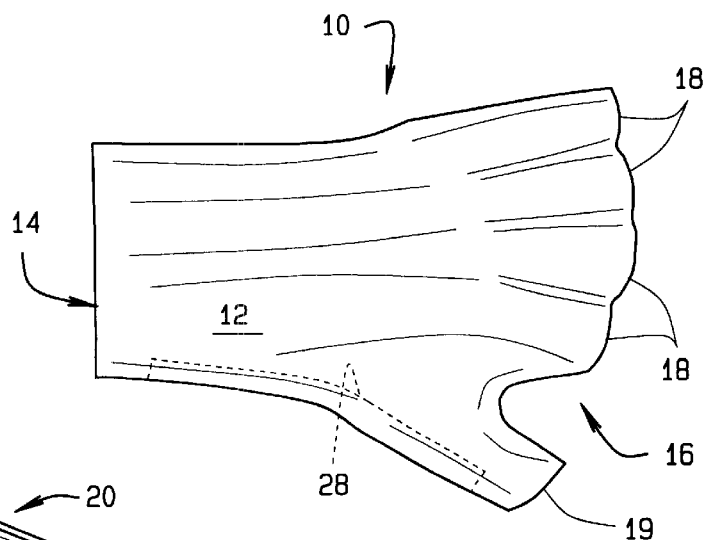
FIG. 2 is a plan view of the brace.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

Referring to the drawings, a dorsal compartment brace 10 of the present invention is designed and constructed to immobilize the first dorsal compartment of a person's hand and wrist. While it important to keep this part of the hand in a fixed position so as not to aggravate an injury to this part of the hand, it is also important to allow movement of the person's thumb and fingers so the person can perform various tasks needed to be done, either as part of rehabilitation of their hand, as well certain normal day-to-day activities.

Unlike previous braces requiring straps or buckles to secure a splint in place at the back of the wearer's hand and wrist, a sleeve 12 of brace 10 comprises a thin, soft, pliable and washable material having an open, upper end 14 sized to fit over the person's arm A. This material can be skin colored so to have a pleasing cosmetic appearance. This makes the brace unobtrusive when worn. The material may also be elasticized for a snug, yet comfortable fit. Since the material is not bulky the splint will fits under the sleeve of a shirt or blouse, or coat or jacket and will not snag on other articles of clothing worn by the wearer. The material is also washable either by hand using soap and water, or in a machine using an appropriate detergent.

The brace does not require straps or other fittings in order to be worn so that the brace can readily be put on and taken off and done so readily and without the need for assistance from another. The overall length of sleeve 12 is such that it extends a distance past the wearer's wrist, but not far up their lower arm. The sleeve is formed so its upper end 14 fits comfortably, yet snugly, over the person's arm. The other end 16 of sleeve 12 has a series of spaced openings 18 formed in it. These openings are sized for the wearer's fingers F to fit through this end of the sleeve. As shown in the drawings, the openings 18 for the fingers allow the fingers to fit through the brace up to the base of each finger. However, the brace 10 further has an open ended extension 19 formed at its end 16. Thumb T fits through this extension 19 which extends partway along the length of the thumb, covering the thumb up to its first joint.

Figure 3A:
FIGS. 3A and 3B are perspective and plan views accordingly of a splint worn as part of the brace.
Figure 3B:
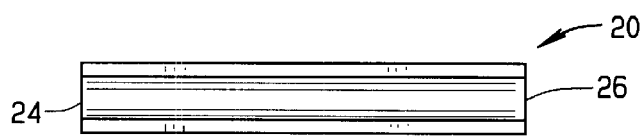

A stiffening member or splint 20 is fitted into brace 10 to immobilize the first dorsal compartment at the back of the hand and wrist on which the brace is worn. The splint is shown in FIGS. 3A and 3B as being generally U-shaped in cross-section with the splint being contoured to fit over the first dorsal compartment portion of the wearer's hand. The splint is also to shown to curve or bend outwardly from a wrist end portion 24 of the splint to an end 26 of the splint fitting about the outside of the person's thumb. Those skilled in the art will understand that as part of the fitting process of brace 10 to the wearer, splint 20 can be custom fitted. Preferably the splint is of a metal, rubber, or plastic construction which, while workable to contour the splint to the wearer's hand, is sufficiently strong to support and immobilize movement of the dorsal portion of the hand after the brace is fitted. Once fitted, neither the brace nor the splint requires further adjustment for proper support of the first dorsal compartment portion of the hand. Thus, straps, wires, and other parts employed on prior art braces are not required on the brace of the present invention to provide the immobilization necessary to promote healing of the hand.

A pocket 28 is formed on the side of sleeve 12. The pocket corresponds in length to the length of splint 20 and extends substantially the length of the sleeve. One end of the pocket begins adjacent wrist end 14 of the sleeve. The pocket extends along the portion of the sleeve covering the backside of the wearer's hand and terminates on extension 19 of end 16 of the sleeve. This end of the pocket is thus between the base of thumb T and the first joint on the thumb. After splint 20 is fitted to the wearer, it is inserted in the pocket and the pocket is sealed by sewing or gluing the open mouth of the pocket closed to hold splint 20 in place. Alternatively, rather than using a splint 20 in the brace, pocket 28 comprises an inflatable pocket. In this construction, the pocket is formed so when filled with air, the pocket fits about the contour of the wearer's hand. The air pressure to which the pocket is inflated is sufficiently high that when the brace is being worn, the first dorsal compartment of the wearer's hand is still immobilized; although, the wearer can still use his or her thumb and fingers for normal activities. In addition to air, other ways of providing a splint include a gel or foam injected into pocket 28 and allowed to set. In this embodiment, the wearer may be wearing the brace during the time it takes for the foam or gel to harden, so that the material, once set, conforms to the contour of the wearer's hand.

As noted, the brace is easy to put on and remove. The elasticized mater from which the sleeve is made fits snugly over the person's arm and the finger holes 18 allow the person to insert his thumb and fingers into the other end of the brace. Because of its relatively compact size, the brace can be conveniently stored.

In view of the above, it will be seen that the several objects and advantages of the present invention have been achieved and other advantageous results have been obtained.

I claim:

1. An orthotic brace for immobilizing a first dorsal compartment on a person's hand comprising:

a sleeve open at one end and sized to fit over the person's arm and extend up the person's forearm a distance above their wrist;

the sleeve being closed at its other end but with openings therein through which the thumb and fingers of the person's hand extend; and, a stiffening member carried by the sleeve and positioned along, the dorsal edge of the person's hand when the sleeve is worn, the stiffening member immobilizing a first dorsal compartment of the person's hand so it cannot move thereby to facilitate healing of an injury to this part of the hand, the stiffening member being a curved splint which is generally U-shaped in cross section along its length and contoured to fit over the first dorsal compartment portion of the person's hand, the splint curving outwardly from a wrist end portion of the splint to an end of the splint fitting about the outside of the person's thumb.

2. The orthotic brace of claim 1 further including a pocket formed on one side of the sleeve, the splint being inserted in the pocket.

3. The orthotic brace of claim 1 wherein the splint is a metal splint which is workable to contour the splint to the wearer's hand, but sufficiently strong to support and immobilize movement of the dorsal portion of the hand when the brace is being worn.

4. The orthotic brace of claim 1 wherein the splint is a rubber splint which is workable to contour the splint to the wearer's hand, but sufficiently strong to support and immobilize movement of the dorsal portion of the hand when the brace is being worn.

5. The orthotic brace of claim 1 wherein the splint is a plastic splint which is workable to contour the splint to the wearer's hand, but sufficiently strong to support and immobilize movement of the dorsal portion of the hand when the brace is being worn.

6. The orthotic brace of claim 2 wherein the sleeve has a thumb extension formed at its closed end, the thumb extension extending a distance above the base of the thumb to approximately the first joint of the thumb, the extension having an opening in the outer end thereof for insertion of the thumb through the extension.

7. The orthotic brace of claim 6 wherein the pocket extends along a back, outer portion of the brace from said one end of the sleeve, along the portion of the sleeve covering the backside of the wearer's hand, and terminates on the extension between the base of the person's thumb and the first joint on the thumb.

8. The orthotic brace of claim 6 wherein the pocket is an inflatable pocket filled with air, the pocket fitting about the contour of the wearer's hand, and the air pressure to which the pocket is inflated being sufficiently high that when the brace is worn, the first dorsal compartment of the wearer's hand is immobilized.

9. The orthotic brace of claim 6 wherein the pocket is filled with a gel material which is injected into the pocket and allowed to set, the gel, when hardened, conforming to the contour of the wearer's hand and immobilizing the first dorsal compartment of the wearer's hand.

10. The orthotic brace claim 6 wherein the pocket is filled with a foam material which is allowed to set, the foam, when hardened, conforming to the contour of the wearer's hand and immobilizing the first dorsal compartment of the wearer's hand.

* * * * *